US005773633A

United States Patent [19]
Kissinger

[11] Patent Number: 5,773,633
[45] Date of Patent: Jun. 30, 1998

[54] PROCESS FOR CRYSTALLIZING CHROMAN-I FROM AN IMPURE MIXTURE

[75] Inventor: Gaylord Michael Kissinger, Evansville, Ind.

[73] Assignee: General Electric Company, Pittsfield, Mass.

[21] Appl. No.: 509,890

[22] Filed: Aug. 1, 1995

[51] Int. Cl.$^6$ .................................................. C07D 311/58
[52] U.S. Cl. ............................................................. 549/406
[58] Field of Search ............................................. 549/406

[56] References Cited

U.S. PATENT DOCUMENTS 3,825,562  7/1974  General Electric Co. ........... 260/345.2
4,240,968  12/1980  General Electric Co. ........... 260/345.2

FOREIGN PATENT DOCUMENTS 246681  10/1987  Czechoslovakia .

OTHER PUBLICATIONS

Lubos Konecny, CA 110:7835, (1989).

*Primary Examiner*—Johann Richter
*Assistant Examiner*—Laura L. Stockton

[57] ABSTRACT

A process is employed for the isolation and crystallization of chroman-I from an impure mixture, by heating the crude mixture, mixing acetone with the hot mixture to obtain a solids-free solution and crystallizing the chroman-I from the solution. Repeated cycles of the process yield high purity chroman-I in good yield.

8 Claims, 1 Drawing Sheet

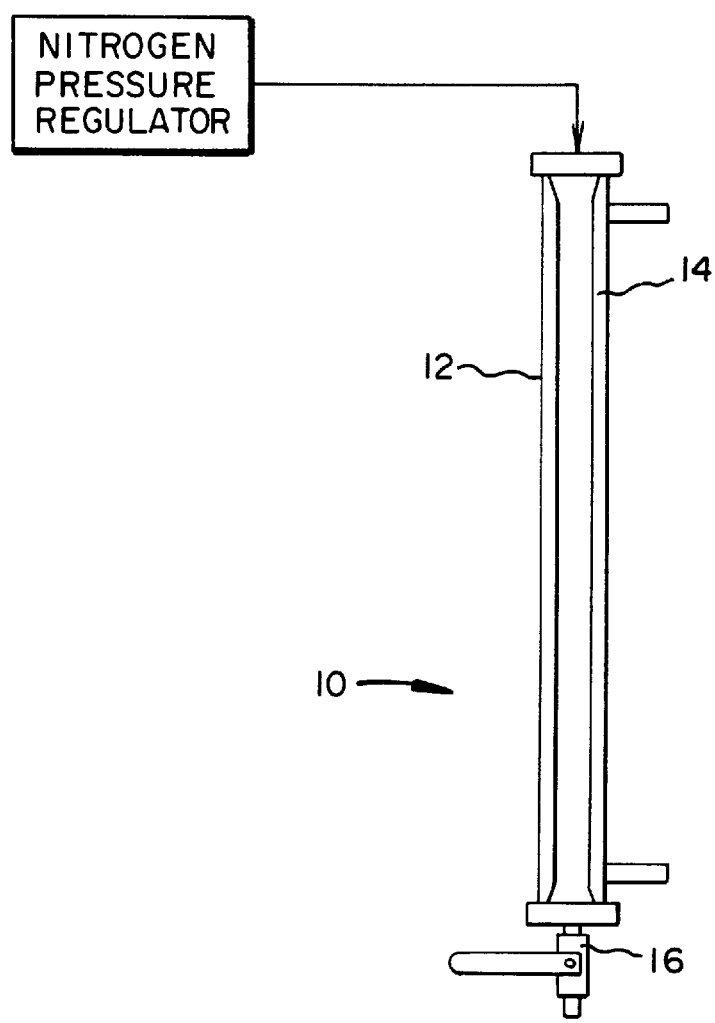

PROCESS FOR CRYSTALLIZING CHROMAN-I FROM AN IMPURE MIXTURE

DETAILED DESCRIPTION OF THE PREFERRED EMBODIMENTS OF THE INVENTION

Those skilled in the art will gain an appreciation of the invention from a viewing of the accompanying drawing in conjunction with a reading of the following description of preferred embodiments of the invention.

BRIEF DESCRIPTION OF THE DRAWINGS

Referring first to the drawing, a process of the invention will be described. The drawing is a schematic depiction of apparatus 10 for the separation and purification of chroman-I, as obtained in the crude product mixture obtained from preparation of bisphenol-A (hereinafter referred to at times for convenience as "BPA") by the condensation of phenol with acetone.

The crude product mixture, containing Chroman-1, (with a composition profiled in Table-1 below), is mixed with acetone. It is important that the mixture be carried out so as to result in a "clear" solution with no solid particles or crystals visually observed. If necessary the solution may be filtered to remove any solids resistant to dissolution.

One convenient method of forming this solution, is to place a known quantity of the crude mixture containing chroman-I into a column (12) as depicted in the accompanying drawing. The column (12) is heated from its jacket (14) to a temperature above that required for the saturation level of any mixture component, (generally 110° C. to 180° C.), preferably around 120° to 140° C.

A quantity of acetone, from about 10 to 30% by weight, is then added to the crude mixture from the bottom of the column (12) of hot crude liquid. Since the temperature is above the boiling point of the crude mixture containing acetone, nitrogen pressure is applied (preferably up to about 15 psig) to the top of the column (12) as a blanket and so as to exceed the partial pressure of the acetone solvent. This effectively prevents boiling of the liquid crude mixture/acetone solution.

Once the solution is formed in column (12) containing the added amount of acetone, and at a temperature high enough to prevent the formation of any crystals (usually between about 100° to 120° C.), the temperature is reduced to about 1° to 2° C. below the nucleation temperature at which crystals of chroman-I will be formed (the nucleation temperature must be determined experimentally for a given solution, since the quantity of acetone, and the chroman-I content of the starting crude mixture can vary).

Once nucleation has occurred, in which small chroman-I crystal nuclei appears, the temperature is then incrementally ramped downward slowly in a controlled manner, advantageously at a rate from about 0.01 to about 1.0 degrees C./minute, to a bottom temperature of from about 25 to 50 degrees C., depending on the desired yield and purity desired from the separation.

During the cooling cycle, the solution is continually saturated with the chroman-I/acetone clathrate, and large, pure crystals are grown inside the crystallizer column (12). These crystals generally range in size (average diameter) of from about 5000 to about 20000 microns.

Controlled (slow) nucleation and controlled (slow) crystal growth rate are essential in changing the crystal morphology, and therefore the effectiveness of this separation method.

Following a brief holding time period at the bottom temperature, the drain valve (16) of column (12) is opened, and the mother liqueur residue is allowed to drain away, leaving purified crystals of chroman-I in the column (12).

Since some of the mother liqueur residue adheres to the chroman-I crystal surfaces in the column (12), the temperature is now raised to an effective level, usually about 120° to 155° C. To bring about a partial melting, or "sweating" of the crystals, during which the amount of liquid residue adhering to the crystal surfaces is removed, resulting in higher purity of the chlathrate crystals suspended in the column (12). This sweat liquor can be separated, or combined with the previously separated mother liqueur, depending on desired purity and yield.

This process can be operated as a single stage, or the process can be repeated in a multi-stage fashion, depending on the desired purity, recycling the separated mother liqueur through the recrystallized steps for added yields and purity. The following Examples are all one stage separations. One skilled in the art can readily see that repeated crystallizations by recycle of the sweat liqueur will bring about substantially higher purity, if desired.

When ultra purity is desired, the chroman-I crystals produced by the process of the invention may be further purified by conventional crystallization processes such as the prior art Melt Crystallization procedures.

The following examples and preparations describe the manner and process of carrying out the invention and set forth the best mode contemplated by the inventor. In the following examples, the apparatus 10 described above and shown in the drawing was employed.

EXAMPLE 1

A quantity of 210,54 grams of starting material was charged to a crystallizer column (12). The initial temperature of the column (12) was held at 120° C., while 52.64 grams of acetone (20 wt %) was pumped into the charge through the bottom of column (12). A nitrogen pressure on the top of the column (12) was maintained at 15 psig.

The column (12) temperature was then reduced to 103 degrees C. and held for 30 minutes to allow nucleation, which occurred at a temperature of 103.6° C.

After the 30 minute hold time, the temperature ramp was started to reduce the temperature to 40° C. over a four hour period of time.

After the four hour period, the temperature was held at 40 C for ½ hour, after which the drain valve (16) was opened and 127.87 grams of mother liqueur residue was collected in a one hour drain period.

After the one hour drain, the temperature of column (12) was raised to 140° C. and held at that temperature for 45 minutes. During this sweating time, 33.78 grams of "sweat" liquor was drained off and collected.

After the 45 minute "sweat" period, the column was heated rapidly to 180° C. 70.76 grams of "melt" was collected as the crystals remaining in the column (12) melted down. Liquid chromatographic analysis of the starting crude mixture, the mother liqueur residue, the sweat and the melt is set forth in Table 1, below.

TABLE 1

| Wt % | Start Mat'l | Residue | Sweat | Melt |
|---|---|---|---|---|
| phenol | NDA | 0.22 | NDA | NDA |
| Ipp | 0.50 | 0.40 | 0.64 | 0.06 |
| p,p'BPA | 0.61 | 0.96 | 0.47 | 0.18 |
| o,p'BPA | 48.82 | 74.16 | 39.43 | 13.33 |
| Ipp Dimers | 0.13 | 0.35 | 0.18 | NDA |
| BPX-I | 1.87 | 2.97 | 1.59 | 0.44 |
| Chroman-1 | 38.57 | 6.22 | 47.47 | 83.39 |
| Spiro-biindane | 0.16 | 0.25 | 0.14 | 0.05 |
| BPX-II | 0.76 | 1.19 | 0.63 | 0.21 |
| Unknowns | 8.59 | 13.28 | 9.44 | 2.34 |
| Total | 100.00 | 100.00 | 100.00 | 100.00 |
| Wt % Acetone | 20.00 | 22.13 | 0.58 | NDA |
| Grams | 210.54 | 99.57 | 33.58 | 70.76 |
| Isomer Grams | 52.64 | 28.30 | 0.20 | 0.00 |
| Acetone Grams Total | 263.18 | 127.87 | 33.78 | 70.76 |

Note: 24.14 grams acetone lost by evaporation.

EXAMPLE 2

216.77 grams of starting material was added to the crystallizer column (12). The initial temperature was held at 120° C., while 72.26 grams of acetone (25 wt %) was pumped into the liquid from the bottom of column (12). The nitrogen pressure on the column top was maintained at 15 psig.

The temperature was then immediately reduced to 103° C. and held for 30 minutes to allow nucleation, which occurred at 103.6° C.

After the 30 minute hold time, a temperature ramp was started from 103° to 30° C., over a four hour period.

After the four hour period, the temperature was held at 30° C. for ½ hour, after which the drain valve (16) was opened and 142.74 grams of mother liqueur residue was drained and collected in a one hour period.

After the one hour drain, the temperature of column (12) was raised to 140° C. and held for 45 minutes. During this time, 26.36 grams of "sweat" liquor was drained and collected.

After the 45 minute "sweat" period, the column was heated rapidly to 180° C., 77.94 grams of "melt" was collected as the crystals in the column (12) melted.

Liquid chromatographic analysis of the starting crude mixture, the mother liqueur residue, the sweat and the melt is set forth in the Table 2, below.

TABLE 2

| Wt % | Start Mat'l | Liqueur Residue | Sweat | Melt |
|---|---|---|---|---|
| phenol | NDA | 0.21 | NDA | NDA |
| Ipp | 0.50 | 0.39 | 0.27 | 0.05 |
| p,p'BPA | 0.61 | 1.04 | 0.73 | 0.23 |
| o,p'BPA | 48.82 | 74.47 | 61.19 | 11.96 |
| BPX-I | 1.87 | 3.00 | 2.38 | 0.44 |
| Chroman-1 | 38.57 | 5.32 | 23.07 | 84.92 |
| Spiro-biindane | 0.16 | 0.26 | 0.20 | 0.05 |
| BPX-II | 0.76 | 1.22 | 0.99 | 0.18 |
| Unknowns | 8.59 | 13.68 | 10.86 | 2.23 |

TABLE 2-continued

| Wt % | Start Mat'l | Liqueur Residue | Sweat | Melt |
|---|---|---|---|---|
| Total | 100.00 | 100.00 | 100.00 | 100.00 |
| Wt % Acetone | 25.00 | 24.20 | 1.55 | NDA |
| Grams | 216.77 | 108.20 | 25.95 | 77.95 |
| Isomer Grams | 72.26 | 34.54 | 0.41 | 0.00 |
| Acetone Grams Total | 289.03 | 142.74 | 26.36 | 77.95 |

Note: 37.31 grams acetone lost by evaporation.

EXAMPLE 3

241.44 grams of starting material was added to the crystallizer column (12). The initial temperature was held at 120° C., while 80.48 grams of acetone (25 wt %) was pumped into the liquid from the column (12) bottom. The nitrogen pressure on the column top was maintained at 15 psig.

The temperature was then immediately reduced to 103° C. and held for 30 minutes to allow nucleation, which occurred at 103.5° C.

After the 30 minute hold time, a temperature ramp was started from 103° to 35° C., over a four hour period.

After the four hour period, the temperature was held at 35° C. for ½ hour, after which the drain valve (16) was opened and 168.25 grams of residue was drained and collected in a ½ hour period.

After the ½ hour period of drain, the temperature was raised to 140° C. and held for 60 minutes. During this time, 33.67 grams of "sweat" liquor was collected.

After the 60 minute "sweat" period, the column was heated rapidly to 180° C. 78.83 grams of "melt" was collected as the crystals in the column melted down. Liquid chromatographic analysis carried out on the crude starting mixture, the mother liqueur residue, the sweat and the melt showed the results set forth in Table 3, below.

TABLE 3

| Wt % | Start Mat'l | Residue | Sweat | Melt |
|---|---|---|---|---|
| phenol | NDA | NDA | NDA | NDA |
| Ipp | 0.50 | 0.21 | 0.16 | NDA |
| p,p'BPA | 0.61 | 0.91 | 0.50 | 0.15 |
| o,p'BPA | 48.82 | 75.06 | 44.68 | 11.37 |
| Ipp Dimers | 0.13 | 0.46 | 0.29 | NDA |
| BPX-I | 1.87 | 3.05 | 1.83 | 0.39 |
| Chroman-1 | 38.57 | 5.61 | 42.07 | 85.93 |
| Spiro-biindane | 0.16 | 0.25 | 0.15 | NDA |
| BPX-II | 0.76 | 1.21 | 0.73 | 0.16 |
| Unknowns | 8.59 | 13.24 | 9.60 | 2.00 |
| Total | 100.00 | 100.00 | 100.00 | 100.00 |
| Wt % Acetone | 25.00 | 26.11 | 1.30 | NDA |
| Grams | 241.44 | 124.33 | 33.23 | 78.83 |
| Isomer Grams | 80.48 | 43.93 | 0.44 | NDA |
| Acetone Grams Total | 321.92 | 168.26 | 33.67 | 78.83 |

Note: 36.11 grams acetone lost by evaporation.

It may be desirable to further purify the chroman-1 for recovery, since it is a valuable material for sale, or for use as a chain terminator in polycarbonate manufacturing.

In the Examples described above, after crystallizing, sweating, and melting the chroman-1 rich fraction, acetone can again be added to the melt, followed by a second crystallization, sweating and melting. This second stage of crystallization can result in very highly purified chroman-1, which when melted, can be crystallized a third time, or it can be flaked or prilled, and collected as a product.

EXAMPLE 4

64.00 grams of starting crude material was charged to the crystallizer column (12). The initial temperature was held at 160° C., while 27.43 grams of acetone (30 wt %) was pumped into the bottom of column (12). The nitrogen pressure on the top of column (12) was maintained at 15 psig.

The temperature was then immediately reduced to 144° C. and held for 30 minutes to allow nucleation, which occurred at 144.7° C.

After the 30 minute hold time, a temperature ramp was started from 145° to 47° C., over a four hour period of time.

After the four hour period, the temperature was held at 47 C for 1 hour, after which the drain valve (16) was opened and 8.22 grams of mother liqueur residue was drained and collected in a ½ our period.

After the ½ hour period of drain, the temperature was raised to 150° C. and held for 60 minutes. During this time, 6.02 grams of "sweat" liquor was drained and collected.

After the 60 minute "sweat" period, the column was heated rapidly to 130° C., 48.61 grams of "melt" was collected as the crystals remaining in the column melted down.

Liquid chromatographic analysis of the crude starting mixture, the mother liqueur, the sweat and the melt gave results shown in Table 4, below.

TABLE 4

| Wt % | Start Mat'l | Liqueur Residue | Sweat | Melt |
|---|---|---|---|---|
| phenol | NDA | NDA | NDA | NDA |
| Ipp | 0.06 | 0.23 | 0.07 | NDA |
| p,p'BPA | 0.18 | 0.67 | 0.38 | 0.09 |
| o,p'BPA | 13.33 | 59.93 | 30.28 | 3.55 |
| Ipp Dimers | NDA | 0.11 | 0.06 | NDA |
| BPX-I | 1.44 | 2.27 | 0.99 | 0.13 |
| Chroman-1 | 83.39 | 24.96 | 62.83 | 95.72 |
| Spiro-biindane | 0.05 | 0.19 | 0.10 | NDA |
| BPX-II | 0.21 | 0.92 | 0.43 | NDA |
| Unknowns | 2.34 | 10.74 | 4.87 | 0.51 |
| Total | 100.00 | 100.00 | 100.00 | 100.00 |

TABLE 4-continued

| Wt % | Start Mat'l | Liqueur Residue | Sweat | Melt |
|---|---|---|---|---|
| Wt % Acetone | 30.00 | 9.71 | 3.21 | 0.94 |
| Grams Isomer | 64.00 | 7.42 | 5.83 | 48.15 |
| Grams | 27.43 | 0.80 | 0.19 | 0.46 |
| Acetone Grams Total | 91.43 | 8.22 | 6.02 | 48.61 |

Note: 36.11 grams acetone lost by evaporation.

What is claimed is:

1. A process for the crystallization of chroman-I from an impure mixture containing the chroman-I, which comprises;

providing a crude mixture containing chroman-I in solution;

heating the crude mixture to a temperature above that required for a the saturation level of any component of the crude mixture;

mixing with the crude mixture, from 10 to 30 percent by weight of the mixture of acetone, whereby a clear solution free of solids is obtained;

reducing the temperature of the solution slowly, to the point where chroman-I crystal nucleation occurs; and reducing the temperature of the nucleated solution at a rate of about 0.01° to about 1.0° C. to a temperature of 25° to 50° C., whereby crystals of chroman-I precipitate from the solution.

2. The process of claim 1 wherein the crude mixture comprises the product obtained upon condensation of phenol with acetone under conditions to obtain bisphenol-A.

3. The process of claim 1 wherein the crude mixture is heated to a temperature within the range of from about 110° C. to about 180° C.

4. The process of claim 1 wherein the precipitated crystals are separated from the solution, which is a mother liqueur.

5. The process of claim 4 wherein the precipitated crystals are warmed to partially melt and exude a sweat.

6. The process of claim 5 wherein the sweat is collected and recycled to the crude mixture.

7. The process of claim 5 wherein the precipitated crystals free of the sweat exudate are melted and recrystallized.

8. The process of claim 7 wherein the melt recrystallized product is further recrystallized.

* * * * *